(12) United States Patent
Lee et al.

(10) Patent No.: US 9,286,681 B2
(45) Date of Patent: Mar. 15, 2016

(54) EDIT GUIDED PROCESSING METHOD FOR TIME-LAPSE IMAGE ANALYSIS

(71) Applicant: DRVision Technologies LLC

(72) Inventors: Shih-Jong James Lee, Bellevue, WA (US); Michael William Jones, Normandy Park, WA (US); Bryce Graff, Kirkland, WA (US)

(73) Assignee: DRVision Technologies LLC, Bellevue, WA (US)

( * ) Notice: Subject to any disclaimer, the term of this patent is extended or adjusted under 35 U.S.C. 154(b) by 57 days.

(21) Appl. No.: 14/297,103

(22) Filed: Jun. 5, 2014

(65) Prior Publication Data
US 2015/0356736 A1 Dec. 10, 2015

(51) Int. Cl.
*G06K 9/03* (2006.01)
*G06T 7/00* (2006.01)
*G06T 7/40* (2006.01)

(52) U.S. Cl.
CPC .............. *G06T 7/0022* (2013.01); *G06T 7/0012* (2013.01); *G06T 7/403* (2013.01); *G06T 2207/10016* (2013.01); *G06T 2207/10056* (2013.01); *G06T 2207/20008* (2013.01); *G06T 2207/30024* (2013.01)

(58) Field of Classification Search
USPC ......... 382/283, 309, 100, 103, 107, 173, 254, 382/224; 345/581, 589, 594, 620, 626; 348/169, 220.1, 231.99, 239, 207.2; 715/833
See application file for complete search history.

(56) References Cited

U.S. PATENT DOCUMENTS

| | | | | |
|---|---|---|---|---|
| 6,111,605 A | * | 8/2000 | Suzuki | H04N 1/00129 348/220.1 |
| 6,380,975 B1 | * | 4/2002 | Suzuki | H04N 1/00129 348/231.99 |
| 6,640,008 B1 | | 10/2003 | Lee et al. | |
| 6,870,945 B2 | * | 3/2005 | Schoepflin | G06T 7/0083 348/169 |
| 7,054,492 B2 | | 5/2006 | Lee et al. | |
| 7,110,603 B2 | | 9/2006 | Lee et al. | |
| 7,446,799 B2 | * | 11/2008 | Suzuki | H04N 1/00129 348/207.2 |
| 7,849,024 B2 | | 12/2010 | Lee et al. | |
| 8,045,783 B2 | | 10/2011 | Lee et al. | |
| 8,209,632 B2 | * | 6/2012 | Reid | G06F 3/04845 345/620 |
| 8,592,919 B2 | * | 11/2013 | Inoue | H01L 29/41725 257/401 |

* cited by examiner

*Primary Examiner* — Anh Do

(57) ABSTRACT

A computerized mask edit guided processing method for time-lapse image analysis performs by a computer program an assisted mask editing on an input image sequence to generate mask edit data, and performs a mask edit guided processing using the image sequence and the mask edit data. A computerized track edit guided processing method for time-lapse image analysis performs by a computer program an assisted track editing on an input image sequence to generate track edit data, and performs a track edit guided processing using the image sequence and the track edit data. A computerized edit guided processing method for time-lapse image analysis performs by a computer program a combination of assisted mask editing and assisted track editing on an input image sequence to generate edit data, and performs a combination of mask edit guided processing and track edit guided processing using the image sequence and the edit data.

21 Claims, 3 Drawing Sheets

EDIT GUIDED PROCESSING METHOD FOR TIME-LAPSE IMAGE ANALYSIS

STATEMENT AS TO RIGHTS TO INVENTIONS MADE UNDER FEDERALLY SPONSORED RESEARCH AND DEVELOPMENT

This work was supported by U.S. Government grant number 5R44HL106863-03, awarded by the National Heart, Lung, and Blood Institutes. The U.S. Government may have certain rights in the invention.

BACKGROUND OF THE INVENTION

1. Field of the Invention

The present invention relates to computerized time-lapse image analysis. More particularly, the present invention relates to (1) computerized mask edit guided processing method for efficient time-lapse image mask editing, (2) computerized track edit guided processing method for efficient time-lapse image track editing, and (3) computerized edit guided processing method for efficient time-lapse image mask and track editing.

2. Description of the Related Art a. Description of Problem that Motivated Invention The technology advancement has enabled the routine acquisition of movie (image sequences) from not only video cameras but also smart phones. Therefore, the demand for time-lapse (rather than fixed point) image analysis becomes more prevalent. In the bioscience field, the advent of time-lapse microscopy and live cell fluorescence probes has enabled biologists to visualize the inner working of living cells in their natural context. Expectations are high for breakthroughs in area such as cell response and motility modification by drugs, control of targeted sequence incorporation into the chromatin for cell therapy, spatial-temporal organization of the cells and its changes with time or under infection, assessment of pathogens routing into the cell, interaction between proteins, and sanitary control of pathogen evolution, etc. The breakthroughs could revolutionize the broad fields in basic research, drug discovery and disease diagnosis.

Deciphering the complex machinery of cell function and dysfunction necessitates a detailed understanding of the dynamics of proteins, organelles, and cell populations. Due to the complexity of the time-lapse image analysis tasks to cover the wide range of highly variable and intricate properties of biological material, it is difficult to have fully automated solutions except some dedicated high-volume applications such as cancer screening, wafer defect inspection. The first and the most critical step of time-lapse image quantification includes objects of interest mask detection and object tracking.

After tackling the huge complexities involved in establishing a live cell imaging study, scientists are often frustrated by the difficulties of image quantification that requires tedious manual operations or semi-automatic processing to achieve the objects of interest mask detection and object tracking. It is highly desirable to have smart editing methods that can efficiently create desired masks and tracks. Furthermore, it is desirable to have the edit results to improve automatic mask detection and object tracking results without the requirement of any image processing knowledge.

b. How Did Prior Art Deal with the Problem?

The prior art approach provides basic manual analysis tools or basic manual editing tools. However, the tools become impractical for time-lapse image analysis, as the data volume is high and the errors could accumulate over time. For example, in time-lapse image sequence tracking applications, a wrong track assignment in the early frame will propagate to the later frames. This causes significant inefficiency for a user to review and correct the mistakes, as the same mistakes have to be repeatedly corrected.

Furthermore, for a meaningful spatial-temporal analysis, the time-lapse image sequence has to cover a long time duration which has high data volume that requires the timely review and correction of analysis error or timely updates of the processing instructions (recipes) to achieve good outcome efficiently. The prior art tools do not satisfy the above requirements.

BRIEF SUMMARY OF THE INVENTION

The primary objective of this invention is to provide a computerized mask edit guided processing method for efficient time-lapse image mask editing and for users to improve mask processing recipe and parameters using edit without any image processing knowledge. The secondary objective of the invention is to provide a computerized track edit guided processing method for efficient time-lapse image track editing and for users to improve track processing recipe and parameters using edit without any image processing knowledge. The third objective of the invention is to provide a computerized edit guided processing method for efficient time-lapse image mask and track editing and for users to improve mask and track processing recipe and parameters using edits without any image processing knowledge. The fourth objective of the invention is to allow users to optimize time-lapse image processing recipe parameters for individual frames through edit guidance. The fifth objective of the invention is to allow the recording of processing update histories.

The current invention provides an edit guided processing framework to assists editing for efficient editing outcomes. It also provide edit guided processing using edit results to improve automatic mask detection and object tracking results without further user involvement. Therefore a user could use edit as the means to improve processing recipe and parameters without any image processing knowledge. Furthermore, the edit guided processing can be logged in processing histories for record archiving and for future references.

DETAILED DESCRIPTION OF THE INVENTION

I. Application Scenarios

Figure 1:
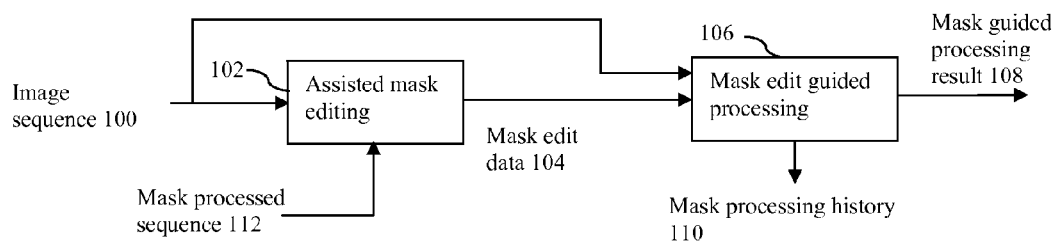
FIG. 1 shows the processing flow of the computerized mask edit guided processing method.

FIG. 1 shows the processing flow of the computerized mask edit guided processing method. An input image sequence 100 is loaded into a computer memory for an assisted mask editing 102 performed by a computer program. The assisted mask editing step 102 processes the input image sequence 100 to generate a mask edit data 104 that stores the mask edited results of the image sequence 100. The mask edit data 104 and the input image sequence 100 are processed by a mask edit guided processing step 106 to generate the mask guided processing result 108. In one embodiment of the invention, the mask edit guided processing step 106 outputs a mask processing history 110 that contains the history of the mask edit guided processing. In an alternative embodiment of the invention, a mask processed sequence 112 is also inputted. In this case, the assisted mask editing 102 does not have to be done from scratch manually. It can be done by altering the masks in the mask processed sequence 112, wherein the mask processed sequence 112 can be generated automatically to improve the overall efficiency.

Figure 2:
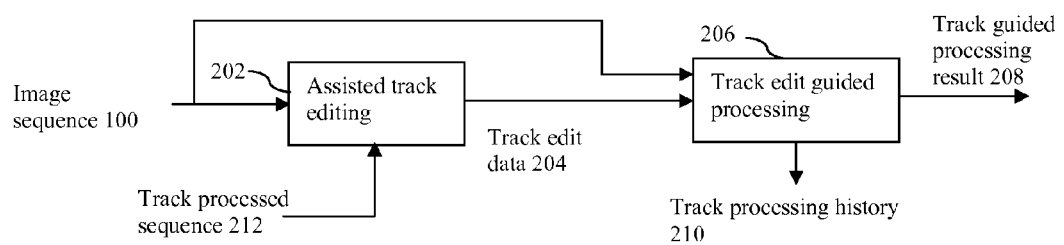
FIG. 2 shows the processing flow of the computerized track edit guided processing method.

FIG. 2 shows the processing flow of the computerized track edit guided processing method. An input image sequence 100 is loaded into a computer memory for an assisted track editing 202 performed by a computer program. The assisted track editing step 202 processes the input image sequence 100 to generate a track edit data 204 that stores the track edited results of the image sequence 100. The track edit data 204 and the input image sequence 100 are processed by a track edit guided processing 206 to generate track guided processing result 208. In one embodiment of the invention, the track edit guided processing step 206 outputs a track processing history 210 that contains the history of the track edit guided processing. In an alternative embodiment of the invention, a track processed sequence 212 is also inputted. In this case, the assisted track editing 202 does not have to be done from scratch manually. It can be done by altering the tracks in the track processed sequence 212, which could be generated automatically to improve the overall efficiency.

Figure 3:
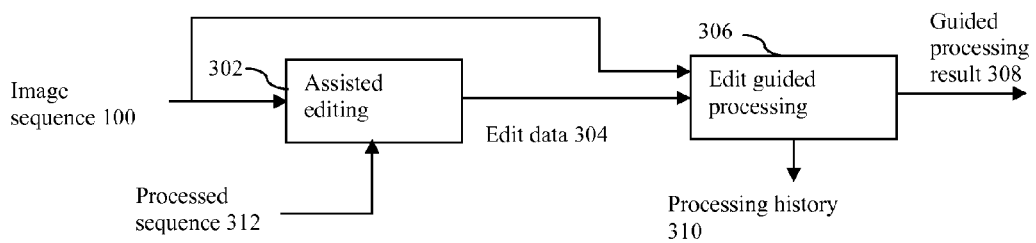
FIG. 3 shows the processing flow of the computerized edit guided processing method.

FIG. 3 shows the processing flow of the general computerized edit guided processing method. An input image sequence 100 is loaded into a computer memory for an assisted editing 302 performed by a computer program. The assisted editing step 302 processes the input image sequence 100 to generate an edit data 304 that stores the edited results of the image sequence 100. The edit data 304 and the input image sequence 100 are processed by an edit guided processing 306 to generate guided processing result 308. In one embodiment of the invention, the edit guided processing step 306 outputs a processing history 310 that contains the history of the edit guided processing. In an alternative embodiment of the invention, a processed sequence 312 is also inputted. In this case, the assisted editing 302 does not have to be done from scratch manually. It can be done by altering the processed sequence 312 that could be generated automatically to improve the overall efficiency. The assisted editing 302 performs a combination of assisted mask editing 102 and assisted track editing 202. Similarly, the edit guided processing 306 performs a combination of mask edited guided 106 processing and track edited guided processing 206.

II. Assisted Mask Editing

Figure 4:
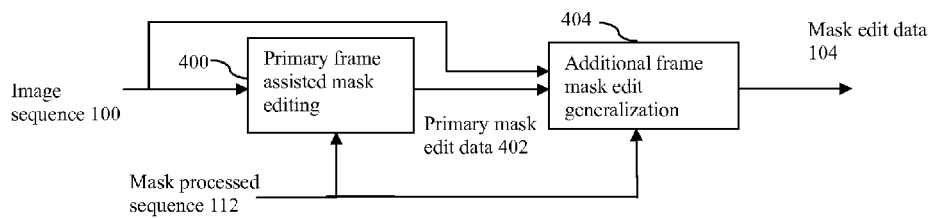
FIG. 4 shows the processing flow of the assisted mask editing method.

The assisted mask editing 102 improves the efficiency of the mask editing so a user can quickly create mask edit data 104. FIG. 4 shows the processing flow of the assisted mask editing method. A primary frame assisted mask editing step 400 processes the input image sequence 100 to generate a primary mask edit data 402. The image sequence 100 and the primary mask edit data 402 are processed by an additional frame mask edit generalization step 404 to generate the mask edit data 104.

A. Input Image Sequence

The input image sequence 100 can be acquired from any digitization method such as a camera, a smart phone, a scanner, photomultipliers, and image sensors, etc. The images can be acquired with different spectral and modalities such as bright field, dark field, X-ray, IR, ultrasound, lasers, etc. as time-lapse (X, Y, T) sequence. It could also include Z dimension (3D) and multiple spectral.

In one embodiment of the invention, microscopy images are used as the input image sequence 100. The microscopy images can be acquired from different microscopy modes such as Total internal reflection fluorescence microscopy (TIRF), bright field, Phase contrast, Differential interference contrast (DIC) microscopy, FRAP, FLIM and FRET, and also could be from 2D and 3D microscopy such as inverted, confocal and super-resolution microscopes.

B. Primary Frame Assisted Mask Editing

Given a frame, the primary frame assisted mask editing 400 assists a user to create and edit masks efficiently through computer assistance. For mask editing, a user can create and/or edit masks using drawing tools such as line tool, curve tool, region tool, polygon tool, circle/ellipse tool and free hand tool, etc. After drawing, the created region or shape can be added to or removed from the mask in the image. The primary frame assisted mask editing 400 improves the region and/or shape creation process so a user can easily create the intended region and/or shape. In one embodiment of the invention, the assisted mask editing 400 performs semi-automatic or automatic shape completion, including region completion and trace following.

1. Region Completion

Region completion could be implemented using the scheme such as Photoshop's Magic Wand Tool. When a user clicks on an area in the primary frame image, region completion looks at the pixel value (tone and color) of the clicked area and selects contiguous pixels that share the same pixel values or pixel values within a tolerance range. In another embodiment of implementation, region completion could be implemented based on shapes or by detecting object edges or by local thresholding. A user can draw a partial boundary of a region, the region completion module will automatically detect the edges and/or equal intensity profile along the user drawn partial boundary and attempts to complete the region or shape/curve for the user. Users could use the boundary suggested by region completion module or continue to draw their owner regions.

2. Trace Following

In the case that a user intends to create a curve such as an arbor of a neuron, the trace following module performs automatic tracing for the user. In one embodiment of the invention, a user draws a starting point of a trace and the trace following module will perform tracing by either brightness tracing or edge tracing. The tracing could go either in one direction (one side from the starting point), two directions (both sides from the starting point) or multiple directions using the starting point as the center. In another embodiment of the invention, a user draws a starting and an end point of the curve and the trace following module traces the curve(s) between the two points. In yet another embodiment of the invention, a user draws a partial curve and the trace following module completes the curve. A user can always revise or ignore the automatically completed curve from the trace following module.

C. Additional Frame Mask Edit Generalization

After the primary frame assisted mask editing 400 is performed on a selected primary frame, the primary mask edit data 402 can be used to efficiently perform mask editing for at least one additional frame. In one embodiment of the invention, the additional frames are specified by a user and the additional frame mask edit generalization 404 performs a simple duplication of the primary mask edit data 402 on the at least one additional frame. For a relatively static image sequence, that is, the content of the image frames are similar over different frames, the duplication method will work well. However, for a more dynamic image where image objects shift over different frames, a simple duplication may not work well. In this case, a duplication and position refinement method could work well. In this case, the at least one mask in the primary mask edit data 402 is placed in the additional frame. Then the position of each of the at least one mask is refined. The refinement could be done by extracting the sub-image corresponding to the mask region of interest in the primary frame and using it as a template to search for the best location in the additional frame to place the mask. In the case that the mask region is deformed from the primary frame to the additional frames, a more sophisticated template search method should be used. In one embodiment of the invention, the mask region is deformed by rotation, therefore a rotation invariant template search is used. The mask region can be created for the additional frame using the position and rotation angle determined from the search. Similarly, a scale invariant search can be used to create a mask region for the additional frame that is enlarged or shrunk from the primary frame mask based on the position and scale factor determined from the search. The method can also be applied to both rotation and scale deformation using rotation and scale invariant template search. A rotated and scale adjusted mask region can then be placed to the search determined location in the additional frame. Many search methods are available for use. For example, the search methods described in the following US patents can be used for the purpose: Lee et, al, "Rotation and scale invariant pattern matching method" U.S. Pat. No. 6,640,008, Oct. 28, 2003; Lee et, al, "Fast regular shaped pattern searching" U.S. Pat. No. 7,054,492, May 30, 2006; and Lee et, al, "Fast invariant matching using template decomposition and synthesis" U.S. Pat. No. 7,110,603, Sep. 19, 2006.

Moreover, if mask deformation includes general linear transformation (or affine transformation), the additional frame mask edit generalization method can make a final linear transformation matching at the search determined location and refine the mask region using linear transformation. The primary mask edit data 402 and the data created by the additional frame mask edit generalization 404 together form the mask edit data 104.

III. Mask Edit Guided Processing

Figure 5:
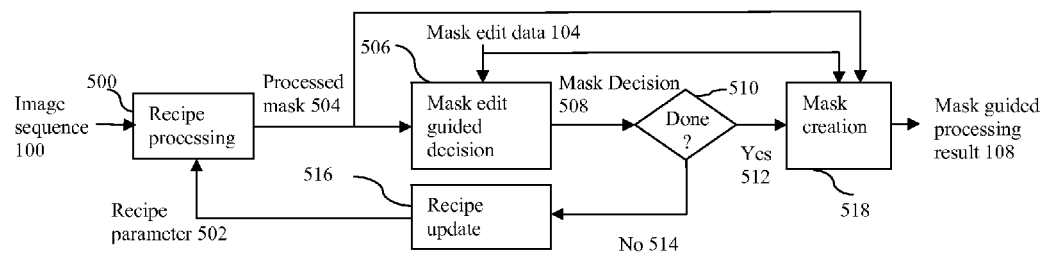
FIG. 5 shows the processing flow of the mask edit guided processing method.

FIG. 5 shows the processing flow of the mask edit guided processing 106. As shown in FIG. 5, the image sequence 100 is processed by a recipe processing step 500 using at least one recipe parameter 502. The recipe processing 500 automatically generates processed mask 504. A mask edit guided decision 506 using the processed mask 504 and the mask edit data 104 to generate a mask decision 508. If the "Done" 510 check using the mask decision 508 is "No" 514, performing a recipe update 516 to update the at least one recipe parameter 502; then recipe processing 500 and mask edit guided decision 506 are repeated. If the "Done" check 510 using the mask decision 508 is "Yes" 512, a mask creation step 518 using the mask edit data 104 and the processed mask 504 is performed to generate mask guided processing result 108.

A. Recipe Processing

A recipe contains instructions for computer image sequence processing for time-lapse image applications such as object tracking, object counting, lineage analysis, exocytosis analysis, colony analysis, etc. The recipe processing steps may contain combinations of operations and parameters (that is, the at least one recipe parameter) selected from a group consisting of enhancement, segmentation, tracking, subset gating, decision, analysis and measurements, etc. In one embodiment of the invention, the recipe can be generated using the method described in Lee et, al, "Imaging system for producing recipes using an integrated human-computer interface (HCI) for image recognition, and learning algorithms" U.S. Pat. No. 7,849,024, Dec. 7, 2010. Using the recipe parameter, the recipe processing step creates processed mask 504.

B. Mask Edit Guided Decision

The mask edit data 104 are treated as truth. The mask edit guided decision 506 compares processed mask 504 generated by the recipe processing 500 and the mask edit data 104. A mask decision 508 is made based on the similarity of the processed mask 504 and the mask edit data 104. In one embodiment of the invention, the mask edit guided decision 506 uses over and under segmentation as the error criteria.

Figures 6A, 6B, 6C:
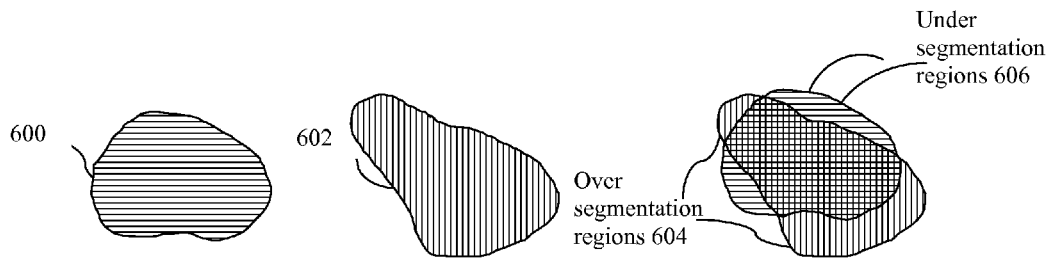
FIG. 6A shows a truth mask from the mask edit data.
FIG. 6B shows the corresponding mask from the processed mask.
FIG. 6C shows the over and under segmentation regions between masks in FIG. 6A and FIG. 6B.

FIGS. 6A-6C illustrate the over and under segmentation regions. FIG. 6A shows a truth mask 600 from the mask edit data 104. FIG. 6B shows the corresponding mask 602 from the processed mask 504. FIG. 6C shows the over segmentation region 604 (indicated by vertical stripe pattern) and under segmentation regions 606 (indicated by horizontal stripe pattern) after overlaying the masks 600 and 602. In one embodiment of the invention, the error metric c is defines as $$\varepsilon = \frac{A_{os} + A_{us}}{A_{truth}}$$

where $A_{os}$ is the area of the over segmentation region; $A_{us}$ is the area of the under segmentation region; and $A_{truth}$ is the area of the truth region. Other criteria includes a variety of functional forms of $A_{os}$, $A_{us}$ and using $A_{truth}$ as normalization factor to suit different applications.

In one embodiment of the invention, the mask decision is the outcome of $\varepsilon < T$, where T is a given tolerance threshold. The "Done" decision is "Yes", when the mask decision is true and the "Done" decision is "No" when the mask decision is false. In another embodiment of the invention, the error metric between recipe update iterations can be tracked, and the "Done" decision is "Yes", when the difference of error metric values between iterations is small or a maximum number of iterations is reached.

C. Recipe Update

Recipe update adjusts recipe parameter to reduce the error metric $\varepsilon$ value such as changing the detection threshold. In one embodiment of the invention, the recipe update step selects from a group consisting of configuration selection, configuration update and parameter update as described in a co-pending US patent application Shih-Jong J. Lee "recipe station for time-lapse image analysis method", application Ser. No. 14/222,657, Mar. 23, 2014. Note that the mask edit guided processing 106 can be applied to each frame independently. That is, the recipe parameters can be updated differently at different frames. The recipe updates and the updated parameters can be logged in the mask processing history 110 for record archiving and for future references.

D. Mask Creation

After recipe is sufficiently updated, the processed mask 504 and mask edit data 104 are integrated by the mask creation step 518 to generate the mask guided processing result 108. In one embodiment of the invention, the mask edit data 104 is considered as truth. Their regions are protected, meaning they have a special priority so they will not be removed or changed. Furthermore, they are used to modify the processed mask 504. For a region in the processed mask 504, if its corresponding region exists in the mask edit data 104, the processed mask region is replaced by the mask edit data 104. In addition, if a region in the processed mask 504 corresponds to a region that is deleted in the mask edit data 104, the processed mask 504 should also be deleted. This results in the mask guided processing result 108.

In an alternative embodiment of the invention, only part of the mask edit data 104 is designated as protected. The designation is done during the assisted mask editing 102. Only the protected mask edit data will be preserved in the mask guided processing result 108.

IV. Assisted Track Editing

Figure 7:
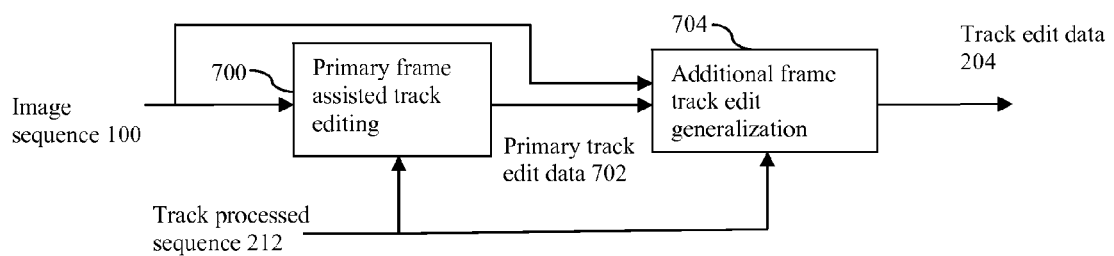
FIG. 7 shows the processing flow of the assisted track editing method.

The assisted track editing 204 improves the efficiency of the track edit so a user can quickly create track edit data 204. FIG. 7 shows the processing flow of the assisted track editing method. A primary frame assisted track mask editing step 700 processes the input image sequence 100 to generate a primary track edit data 702. The image sequence 100 and the primary track edit data 702 are processed by an additional frame track edit generalization step 704 to generate the track edit data 204.

A. Primary Frame Assisted Track Editing

Given a frame or a few frames, the primary frame assisted track editing 700 assists a user to create and edit tracks efficiently through computer assistance. For track editing, a user can create and/or edit tracks using track editing tools. The tool allows a user to modify the state of a track such as Create a new track
Connect tracks
Delete a track point
Delete full track
Extend a track
Move a track point
Connect/disconnect lineage division The primary frame assisted mask editing 700 improves the process of "connect tracks", "extend a track" and "move a track point" operations. In one embodiment of the invention, the assisted track editing 204 performs semi-automatic or automatic location guidance. When connecting two tracks with missing frames between the end frame of track 1 and starting frame of track 2, the assisted track editing 204 will automatically add the track locations for the missing frames. This could be further adjusted by a user using "move a track point" tool. When extending a track, the assisted track editing 204 will automatically advance to the most likely positions of the extended frames and this could be further adjusted by a user using "move a track point" tool. When a user moves a track, a suggested position along the direction where the user is moving toward can be provided by the assisted track editing 204 to assist the user's editing movement.

B. Additional Frame Track Edit Generalization

After the primary frame assisted track editing 700 is performed on a selected primary frames, the primary track edit data 702 can be used to efficiently perform track editing for at least one additional frame. In one embodiment of the invention, the additional frames are specified by a user. The additional frame track edit generalization 704 allows a user to specify a track point at a primary frame and a future frame. It then automatically fills in the track points between the two frames. In one embodiment of the invention, the track point fill-in operation is performed by backward tracking from the future frame back to the primary frame. In another embodiment of the invention, the track point fill-in operation is performed by forward tracking from the primary frame to the future frame. In yet another embodiment of the invention, the track point fill-in operation is performed by a combination of backward tracking from the future frame and forward tracking from the primary frame. If the backward track and forward track meet (coincide) in an in-between frame, the combination is performed by taking backward track after the coinciding frame and forward track up to and including the coinciding frame. If the backward track and forward track do not meet, the closet point and frame between them is determined and a best compromise point is chosen for that frame. Afterwards, the combination can be done by taking backward track after the closet frame and forward track up to and including the closet frame using the compromise point. The compromise point selection could be done manually by a user, that is, a manual revising can be performed. For tracking, the method described in Lee et, al, "Method for moving cell detection from temporal image sequence model estimation" U.S. Pat. No. 8,045,783, Oct. 25, 2011 can be used.

V. Track Edit Guided Processing

As shown in FIG. 2, the image sequence 100 and track edit data 204 are processed by the track edit guided processing step 206 to generate track guided processing result 208. A major step of a tracking process is the match making process. The match making process matches the previous frame track points to the current frame track points. In one embodiment of the invention, the track edit data 204 are treated as true track. They will dynamically affect the match making process. That is, the edited track points are excluded from the list of match making candidates for both previous frames and current frames. This constrains the matching making process to avoid matching mistakes and therefore it effectively improves the tracking accuracy guided by the track edit data 204.

In an alternative embodiment of the invention, the match making parameters are updated to best accomplish the matches specified by the track edit data 204. The updated parameters should yield the lowest matching error with respect to the track edit data 204. Afterwards, the track edit data 204 is considered truth and the edited track points are excluded from the list of match making candidates for both previous frames and current frames. This guarantees the preservation of the track edit data 204 in the track guided processing result 208.

The match making parameters can be updated on all frames where track edit data 204 exists. That is, the tracking recipe parameters can be updated differently at different frames. The recipe updates and the updated parameters can be logged in the track processing history 210 for record archiving and for future references.

VI. Assisted Editing

Figure 8:
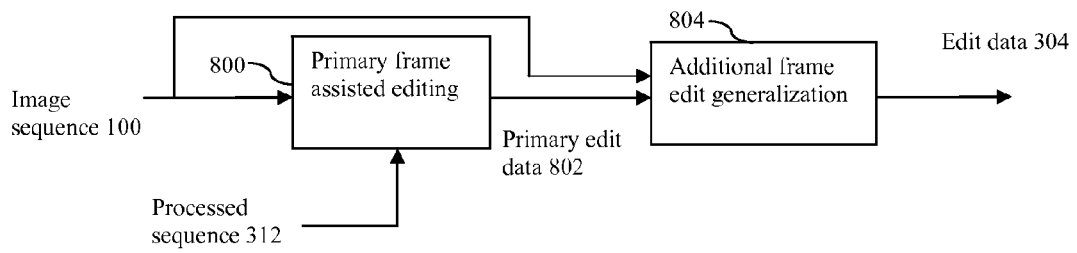
FIG. 8 shows the processing flow of the assisted editing method.

The assisted editing 302 improves the efficiency of the editing so a user can quickly create edit data 304. FIG. 8 shows the processing flow of the assisted editing method. A primary frame assisted editing step 800 processes the input image sequence 100 to generate a primary edit data 802. The image sequence 100 and the primary edit data 802 are processed by an additional frame edit generalization step 804 to generate the edit data 304.

A. Primary Frame Assisted Editing

In one embodiment of the invention, the primary frame assisted editing 800 includes a primary frame assisted mask editing 400 followed by a primary frame assisted track editing 700. In another embodiment of the invention, the primary frame assisted editing 800 includes a primary frame assisted track editing 700 followed by a primary frame assisted mask editing 400. This results in the primary edit data 802.

B. Additional Frame Edit Generalization

In one embodiment of the invention, the additional frame edit generalization 804 includes an additional frame mask edit generalization 404 followed by an additional frame track edit generalization 704. In another embodiment of the invention, the additional frame edit generalization 804 includes an additional frame track edit generalization 704 followed by an additional frame mask edit generalization 404. This results in the edit data 304.

VII. Edit Guided Processing

In one embodiment of the invention, the edit guided processing 306 includes a mask edit guided processing 106 followed by a track edit guided processing 206. In another embodiment of the invention, the edit guided processing 306 includes a track edit guided processing 206 followed by a mask edit guided processing 106. This results in the guided processing result 308. The recipe updates and the updated parameters can be logged in the processing history 310 for record archiving and for future references.

The invention has been described herein in considerable detail in order to comply with the Patent Statutes and to provide those skilled in the art with the information needed to apply the novel methods and to construct and use such specialized components as are required. However, it is to be understood that the inventions can be carried out by specifically different equipment and devices, and that various modifications, both as to the equipment details and operating procedures, can be accomplished without departing from the scope of the invention itself.

What is claimed is:

1. A computerized mask edit guided processing method for time-lapse image analysis, comprising the steps of:
    a) inputting an image sequence into a computer memory;
    b) performing by a computer program in a computerized analysis tool an assisted mask editing using the image sequence stored in the computer memory to generate mask edit data; and
    c) performing a mask edit guided processing in the computerized analysis tool using the image sequence and the mask edit data to generate a mask guided processing result.

2. The computerized mask edit guided processing method of claim 1, wherein the assisted mask editing comprises the steps of:
    a) performing a primary frame assisted mask editing in the computerized analysis tool using the image sequence stored in the computer memory to generate primary mask edit data; and
    b) performing an additional frame mask edit generalization in the computerized analysis tool using the image sequence and the primary mask edit data to generate the mask edit data.

3. The computerized mask edit guided processing method of claim 1, wherein the mask edit guided processing comprises the steps of:
    a) performing a recipe processing in the computerized analysis tool using the image sequence stored in the computer memory and at least one recipe parameter to generate a processed mask;
    b) performing a mask edit guided decision in the computerized analysis tool using the processed mask and the mask edit data to generate a mask decision;
    c) performing a Done check in the computerized analysis tool using the mask decision;
    d) if the Done check result is "No", performing a recipe update in the computerized analysis tool to update the at least one recipe parameter; then repeating from step a); and
    e) if the Done check result is "Yes", performing a mask creation in the computerized analysis tool using the mask edit data and the processed mask to generate the mask guided processing result.

4. The computerized mask edit guided processing method of claim 1, wherein the mask edit guided processing further outputs a mask processing history.

5. The computerized mask edit guided processing method of claim 1, further inputting a mask processed sequence into the computer memory and the assisted mask editing alters masks in the mask processed sequence.

6. The computerized mask edit guided processing method of claim 2, wherein the primary frame assisted mask editing performs a step selected from a group consisting of mask region completion and trace following.

7. The computerized mask edit guided processing method of claim 2, wherein the additional frame mask edit generalization performs, for a selected range of frames, a step selected from a group consisting of:
    Duplication;
    Duplication and position refinement; and
    Duplication and position and shape refinement.

8. The computerized mask edit guided processing method of claim 3, wherein the mask edit guided decision uses over and under segmentation error metric.

9. A computerized track edit guided processing method for time-lapse image analysis, comprising the steps of:
    a) inputting an image sequence into a computer memory;
    b) performing by a computer program in a computerized analysis tool an assisted track editing using the image sequence stored in the computer memory to generate track edit data; and
    c) performing a track edit guided processing in the computerized analysis tool using the image sequence and the track edit data to generate a track guided processing result.

10. The computerized track edit guided processing method of claim 9, wherein the assisted track editing comprises the steps of:
    a) performing a primary frame assisted track editing in the computerized analysis tool using the image sequence stored in the computer memory to generate primary track edit data; and
    b) performing an additional frame track edit generalization in the computerized analysis tool using the image sequence and the primary track edit data to generate the track edit data.

11. The computerized track edit guided processing method of claim 9, wherein the track edit guided processing preserves the track edit data to constrain track match making.

12. The computerized track edit guided processing method of claim 9, wherein the track edit guided processing further outputs a track processing history.

13. The computerized track edit guided processing method of claim 9, further inputting a track processed sequence into the computer memory and the assisted track editing alters tracks in the track processed sequence.

14. The computerized track edit guided processing method of claim 10, wherein the primary frame assisted track editing performs location guidance.

15. The computerized track edit guided processing method of claim 10, wherein the additional frame track edit generalization performs, for a selected range of frames, a step selected from a group consisting of forward tracking, backward tracking, and a combination of backward and forward tracking.

16. A computerized edit guided processing method for time-lapse image analysis, comprising the steps of:
 a) inputting an image sequence into a computer memory;
 b) performing by a computer program in a computerized analysis tool an assisted editing using the image sequence stored in the computer memory to generate edit data; and
 c) performing an edit guided processing in the computerized analysis tool using the image sequence and the edit data to generate a guided processing result.

17. The computerized edit guided processing method of claim 16, wherein the assisted editing comprises the steps of:
 a) performing a primary frame assisted editing in the computerized analysis tool using the image sequence to generate primary edit data; and
 b) performing an additional frame edit generalization in the computerized analysis tool using the image sequence and the primary edit data to generate the edit data.

18. The computerized edit guided processing method of claim 16, wherein the edit guided processing further outputs a processing history.

19. The computerized edit guided processing method of claim 16, wherein the assisted editing performs assisted mask editing and assisted track editing.

20. The computerized edit guided processing method of claim 16, wherein the edited guided processing performs mask edited guided processing and track edited guided processing.

21. The computerized edit guided processing method of claim 16, further inputting a processed sequence into the computer memory and the assisted editing alters the processed sequence.

* * * * *